(12) United States Patent
Seward et al.

(10) Patent No.: US 6,485,425 B2
(45) Date of Patent: Nov. 26, 2002

(54) APPARATUS AND METHOD OF HOLDING AND MANIPULATING SMALL ULTRASOUND TRANSDUCERS

(75) Inventors: James B. Seward, Rochester, MN (US); Charles J. Bruce, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/797,396

(22) Filed: Mar. 1, 2001

(65) Prior Publication Data

US 2001/0031923 A1 Oct. 18, 2001

Related U.S. Application Data

(60) Provisional application No. 60/186,536, filed on Mar. 2, 2000.

(51) Int. Cl.[7] .............................................. A61B 8/14
(52) U.S. Cl. ...................................................... 600/459
(58) Field of Search ........................ 600/459, 462–463, 600/466–467, 471, 453–455, 437, 439

(56) References Cited

U.S. PATENT DOCUMENTS

| | | | | |
|---|---|---|---|---|
| 4,802,487 A | * | 2/1989 | Martin et al. ................ 600/463 |
| 4,926,875 A | | 5/1990 | Rabinovitz et al. |
| 4,972,839 A | * | 11/1990 | Angelsen ..................... 600/462 |
| 5,152,293 A | | 10/1992 | Vonesh et al. |
| 5,178,150 A | * | 1/1993 | Silverstein et al. ......... 600/463 |
| 5,325,860 A | | 7/1994 | Seward et al. |
| 5,345,940 A | | 9/1994 | Seward et al. |
| 5,598,846 A | | 2/1997 | Peszynski |
| 5,671,747 A | * | 9/1997 | Connor ........................ 600/459 |
| 5,695,491 A | * | 12/1997 | Silverstein .................... 606/1 |
| 5,699,805 A | | 12/1997 | Seward et al. |
| 5,704,361 A | | 1/1998 | Seward et al. |
| 5,713,363 A | | 2/1998 | Seward et al. |
| 5,722,403 A | * | 3/1998 | McGee et al. ............... 607/120 |
| 5,775,328 A | * | 7/1998 | Lowe et al. ................. 600/463 |
| 5,792,059 A | | 8/1998 | Furia et al. |
| 6,039,693 A | | 3/2000 | Seward et al. |
| 6,059,731 A | | 5/2000 | Seward et al. |
| 6,099,475 A | | 8/2000 | Seward et al. |
| 6,129,672 A | | 10/2000 | Seward et al. |
| 6,171,247 B1 | | 1/2001 | Seward et al. |

OTHER PUBLICATIONS

Bruce, C. et al., "Intracardiac Doppler Hemodynamics and flow: New Vector, Phase–Array Ultrasound–Tipped Catheter", *The American Journal of Cardiology*, vol. 83, pp. 1509–1512 (May 15, 1999).

Bruce, C. et al., "Transvascular Imaging: Feasibility Study Using a Vector Phased Array Ultrasound Cathether", *Echocardiography: A Jrnl. of CV Ultrasound & Allied Tech.*, vol. 16, No. 5, pp. 425–430 (1999).

(List continued on next page.)

*Primary Examiner*—Francis J. Jaworski
(74) *Attorney, Agent, or Firm*—Merchant & Gould P.C.

(57) ABSTRACT

An apparatus and method for holding and manipulating a miniaturized ultrasound transducer includes a flexible member, a retaining member, and a control member. The miniaturized ultrasound transducer is mounted on the flexible member proximate a distal end of the flexible member. The retaining member retains the flexible member proximate the distal end of the flexible member. The control member is coupled to the retaining member and is operable to move the retained flexible member and ultrasound transducer to optimize ultrasound visualization.

7 Claims, 6 Drawing Sheets

OTHER PUBLICATIONS

Click, RL et al., "Role of Intraoperative Tee and Its Impact on Surgical Decisions, Prospective Review of 2,261 Adult Cases", *Journal of the American Society of Echocardiography*, p. 396 (May 1997).

Freeman, W. et al., "Intraoperative Evaluation of Mitral Valve Regurgiation and Repair by Transesophageal Echocardiography: Incidence and Significance of Systolic Anterior Motion", *JACC*, vol. 20, No. 3, pp. 599–609 (Sep. 1992).

Hung, J. et al., "Usefulness of Intracardiac Echocardiography in Complex Transseptal Catheterization During Percutaneous Transvenous Mitral Commissurotomy", *Mayo Clinic Proceedings*, vol. 71, pp. 134–140 (Feb. 1996).

Kalman, J. et al., "Use of Intracardiac Echocardiography in Interventional Electrophysiology", *PACE*, vol. 20, pp. 2248–2262 (Sep. 1997, Part I).

Kantor, B., "A Novel High–Resolution Intracardiac Echocardiographic Catheter Improves Guidance of Percutaneous Myocardial Revascularization", *The American Journal of Cardiology*, TCT Abstracts/Oral, p. 17S (Oct. 1998).

O'Leary, P., "Biplane Intraoperative Transesophageal Echocardiography in Congenital Heart Disease", *Mayo Clinic Proceedings*, vol. 70, pp. 317–326 (Apr. 1995).

Packer, D.L., "Intracardiac Ultrasound Guidance of Linear Lesion Creation for Ablation of Atrial Fibrillation", *JACC*, p. 333A (Feb. 1998).

Pandian, N., "Intravascular and Intracardiac Ultrasound Imaging An Old Concept, Now on the Road to Reality", *Circulation*, vol. 80, No. 4, pp. 1091–1094 (Oct. 1989).

Segar, D. et al., "Intracardiac Echocardiography–guided Biopsy of Intracardiac Masses", *Journal of the American Society of Echocardiography*, vol. 8, No. 6, pp. 927–929 (Nov.–Dec. 1995)

Seward, J. et al., "Transesophageal Echocardiography: Technique, Anatomic Correlations, Implementation, and Clinical Applications", *Mayo Clinic Proceedings*, vol. 63, pp. 649–680 (Jul. 1988).

Seward, J. et al., "Ultrasound Cardioscopy: Embarking on a New Journey", *Mayo Clinic Proceedings*, vol. 71, No. 7, pp. 629–635 (Jul. 1996).

Wilson, T. et al., "Current Status of Transrectal Ultrasonography in the Detection of Prostate Cancer", *Oncology*, vol. 5, No. 1, pp. 73–78 (Jan. 1991).

Becker, H.D., "Endobronchialer Ultraschall—Eine neue Perspektive in der Bronchologie", *Ultrashall in Med.*, vol. 17, pp. 106–112 (1996).

Walther, V. et al., "Staging of Bladder Tumors by Transuretheral Ultrasound Tomography", *Ultrasound in Medicine and Biology Suppl.*, pp. 535–539 (1983).

\* cited by examiner

APPARATUS AND METHOD OF HOLDING AND MANIPULATING SMALL ULTRASOUND TRANSDUCERS

RELATED APPLICATION

This application claims the benefit of Provisional Application, U.S. Serial No. 60/186,536, filed on Mar. 2, 2000, entitled "CONTROL DEVICES FOR MANIPULATION OF SMALL SURGICAL ULTRASOUND TRANSDUCERS", by James B. Seward and Charles J. Bruce, which is incorporated herewith by reference.

FIELD OF THE INVENTION

The present invention relates to ultrasound transducers, and more particularly, to apparatus and method of holding and manipulating small or minute ultrasound transducers.

BACKGROUND OF THE INVENTION

Ultrasound is a ubiquitous technology capable of obtaining images, assessing functions, measuring hemodynamics, characterizing tissues, visualizing fluid flows, etc. One of the major attributes of ultrasound is its safety, adaptability, low cost, and high spatial and temporal resolution.

As less invasive surgical techniques evolve and the complexity of such procedures increases, direct alternative imaging and control of an event becomes essential. Today, ultrasound is one of the most practical energy sources that can be formulated into small usable devices capable of being manipulated within a surgical environment. Ultrasound can be used as a visual substitute within the opaque confines of body cavities and tissues. Ultrasound vision provides an immediate imaging solution to evaluate the intended result of an intervention.

As a result, ultrasound technology has evolved to be one of the most commonly employed imaging modalities in medical practice. Recent advances include the development of sophisticated multi-array devices, which are of small caliber typically attached by flexible electronics to a fully complemented ultrasound system. Until recently, the applications of small interventional ultrasound transducers have been principally confined to endoscopic applications. Endoscopic devices are rigid or semi-regid scopes, inserted through ports into body cavities (such as esophageal, rectum, vagina, etc.) or vessels. Such devices are rigid enough to be manipulated by hand or self-contained mechanisms.

However, miniaturized or small ultrasound transducer devices are still a recent advent and intend to incorporate ultrasound attributes, such as Doppler, color flow imaging, parametrics, etc. These ultrasound transducer devices are of small caliber, flexible, and incapable of having sufficient internal control. The use of very small caliber ultrasound devices within a body cavity, e.g. a surgical field, has not been previously feasible. There are at least three principal reasons for this reality. Firstly, most early ultrasound devices and transducers were too large or too rigid to accommodate manual and/or digital manipulation within the surgical field or within the appropriate body cavity. Secondly, it is very difficult to control a small or minute transducer. Thirdly, there is insufficient means of controlling the small transducers in the moist confines of a body cavity.

Currently, in a surgery involving the use of ultrasound imaging, a primary surgical physician rarely personally uses ultrasound imaging. Typically, a separate physician outside the immediate surgical environment performs the ultrasound examination. This second physician monitors changes in anatomy, physiology, and procedural outcome and communicates these observations to the primary physician. The primary physician is dependent on a disconnected, and sometimes, unpredictable or unreliable resource. It is desirable to have the primary physician use an imaging device suited for its own specific needs.

Accordingly, there is a need for means of controlling a small ultrasound device, which would allow one to easily manipulate such device in an underfluid environment, particularly in the moist confines of a body cavity. Also, there is a need for a versatile, inexpensive means of controlling such a small device.

SUMMARY OF THE INVENTION

In accordance with this invention, the above and other problems were solved by providing an apparatus and method for holding and manipulating a miniaturized ultrasound transducer.

In one embodiment of the present invention, the apparatus includes: a flexible member, a retaining member, and a control member. The miniaturized ultrasound transducer is mounted on the flexible member proximate a distal end of the flexible member. The flexible member can be a catheter or other types of thin tube carriers. The retaining member retains the flexible member proximate the distal end of the flexible member. The control member is coupled to the retaining member and is operable to move the retained flexible member and the ultrasound transducer to optimize ultrasound visualization.

Further in one embodiment, the retaining member is a clip having a C-shape. The clip retains the flexible member. The control member is a clip having a C-shape. An operator's finger is clipped onto the control member. The backsides of the C-shaped retaining member and control member are integral to each other. The operator's finger controls the movements of the flexible member and the ultrasound transducer mounted thereon.

In another embodiment of the present invention, the retaining member is a semi-rigid tube. The flexible member is inserted through and retained by the semi-regid tube, and the ultrasound transducer is exposed at an end of the semi-rigid tube. The control member includes a plurality of handles and an articulation mechanism. The articulation mechanism is connected to the handles and the flexible member, and the handles are operable to control the movements of the flexible member and the ultrasound transducer.

In another embodiment of the present invention, the retaining member is a hollow tube. The flexible member is inserted through and retained by the hollow tube, and the ultrasound transducer is exposed at an end of the hollow tube. The control member includes a multi-faceted articulated joint and a handle. The handle is connected to the multi-faceted articulated joint and is operable to control the positions of the flexible member and the ultrasound transducer.

In another embodiment of the present invention, the retaining member includes a hollow tube, a handle, a rigid shaft, and a clip. The flexible member is inserted through the hollow tube within the handle and is held in position by the clip affixed to the rigid shaft. The control member includes a trigger mechanism having a trigger and a deflecting cable or wire. The deflecting cable or wire is connected to the flexible member and the trigger. The trigger is operable to control the movements of the flexible member and ultrasound transducer.

In another embodiment of the present invention, the retaining member is a clip having a C shape. The flexible member is inserted into the clip. The control member also includes a pair of suture holes for fixing the retaining member onto a surface. The flexible member is repositionable and/or rotatable within the clip so as to move the ultrasound transducer at will.

One advantage of the present invention is that it allows one to hold and manipulate a very small ultrasound transducer, particularly within a moist surgical field.

Another advantage of the present invention is that it accommodates surgeon's needs, such as the size of a surgeon's hand, etc., and surgeon's ability to reach a specific location and function in an underfluid environment.

A further advantage of the present invention is that it empowers an operator, e.g. a surgeon, to personally and interactively assess the status and result of the operation without having a second operator to perform a separate examination and communicate the results to the operator. Accordingly, the operator is able to assess a personal status and result, thereby giving the imaging capability to the hands of an actual person who performs intervention.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

In the following description of the illustrated embodiments, reference is made to the accompanying drawings that form a part hereof, and in which is shown by way of illustration several embodiments in which the invention may be practiced. It is to be understood that other embodiments may be utilized as structural changes may be made without departing from the spirit and scope of the present invention.

The present invention provides an apparatus for holding and manipulating a miniaturized ultrasound transducer.

FIGS. 1–4 illustrate a first embodiment of an apparatus 40 for holding and manipulating a miniaturized ultrasound transducer 42 in accordance with the principles of the present invention.

Figures 1, 2:
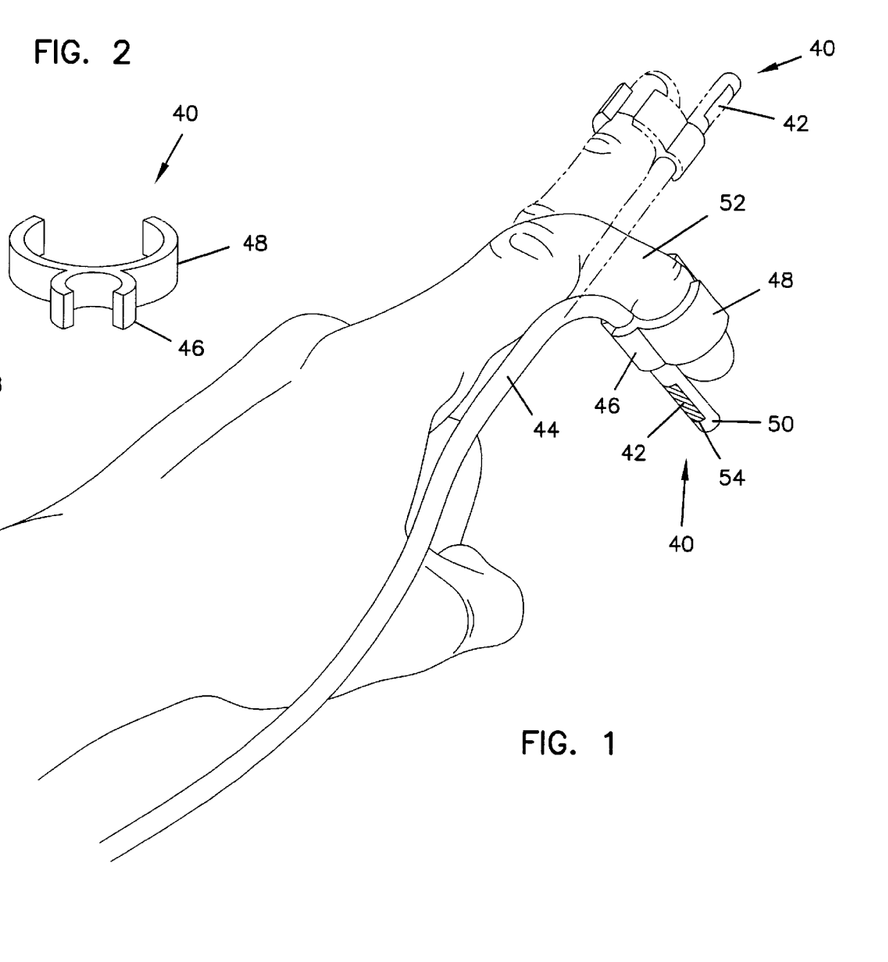
FIG. 1 is a perspective view of a first embodiment of an apparatus for holding and manipulating a miniaturized ultrasound transducer in accordance with the principles of the present invention, the apparatus being operated by an operator's finger.
FIG. 2 is a perspective view of the apparatus of FIG. 1 without showing the operator's finger or the flexible member with the ultrasound transducer mounted thereon.

In FIG. 1, the apparatus 40 includes a flexible member 44, a retaining member 46, and a control member 48. The miniaturized ultrasound transducer 42 is mounted on the flexible member 44 proximate a distal end 50 of the flexible member 44. The retaining member 46 retains the flexible member 44 proximate the distal end 50 of the flexible member 44. The control member 48 is coupled to the retaining member 46 and is operable to move the retained flexible member 44 and ultrasound transducer 42 to optimize ultrasound visualization. As shown, the apparatus 40 is operated by an operator's finger 52 in a bent position (in solid lines) and a straight position (in phantom lines).

It is appreciated that the operator's finger can control the movements of the flexible member 44 and ultrasound transducer 42 mounted thereon in many other positions to optimize ultrasound visualization. Accordingly, the operator is capable of holding the ultrasound transducer 42 in a desired position and manipulating the ultrasound transducer 42 to reach a specific location.

Figures 3, 4:
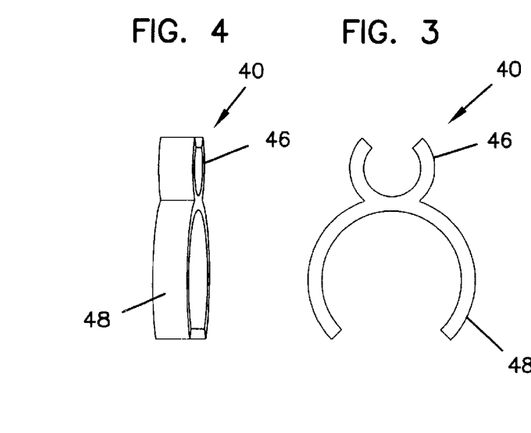
FIG. 3 is a front elevational view of the apparatus of FIG. 1 without showing the operator's finger or the flexible member with the ultrasound transducer mounted thereon.
FIG. 4 is another perspective view of the apparatus of FIG. 1 without showing the operator's finger or the flexible member with the ultrasound transducer mounted thereon.

In FIGS. 2–4, the apparatus 40 is shown without showing the operator's finger 52 or the flexible member 44 with the ultrasound transducer 42 mounted thereon. As shown, the retaining member 46 is a clip having a C-shape or a ring-like structure. The clip 46 secures the flexible member 44 and the ultrasound transducer 42. The control member 48 is also a clip having a C-shape or a ring-like structure. The operator's finger can be clipped onto the control member 48. The backsides of the C-shaped retaining member 46 and control member 48 are integral to each other. The operator's finger 52 controls the movements of the flexible member 44 and the ultrasound transducer 42 mounted thereon.

An exemplary use of the apparatus 40 is shown in FIG. 1. The control member 48 snaps onto the distal phalanx of the finger 52 of the operator. The retaining member 46 secures the flexible member 44 and the ultrasound transducer 42 in position so that an imaging surface 54 of the ultrasound transducer 42 is not blocked or covered, and the apparatus 40 is firmly apposed to the articulating finger 52.

FIGS. 5–10 illustrate a second embodiment of an apparatus 56 for holding and manipulating a miniaturized ultrasound transducer in accordance with the principles of the present invention.

Figure 5:
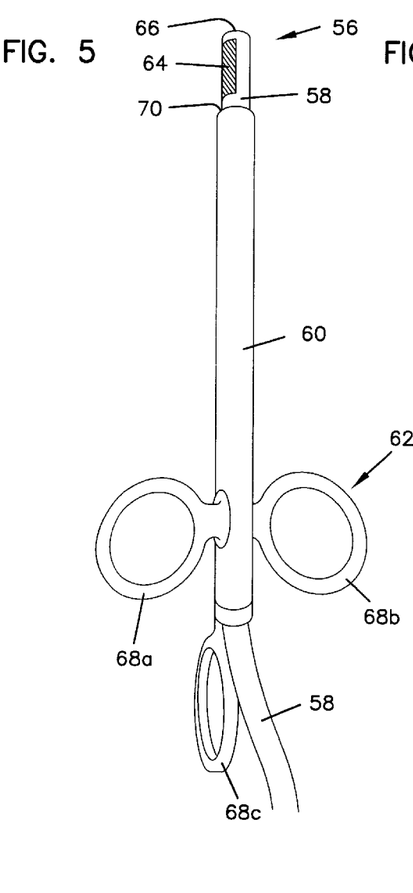
FIG. 5 is a perspective view of a second embodiment of an apparatus for holding and manipulating a miniaturized ultrasound transducer in accordance with the principles of the present invention.
Figure 6:
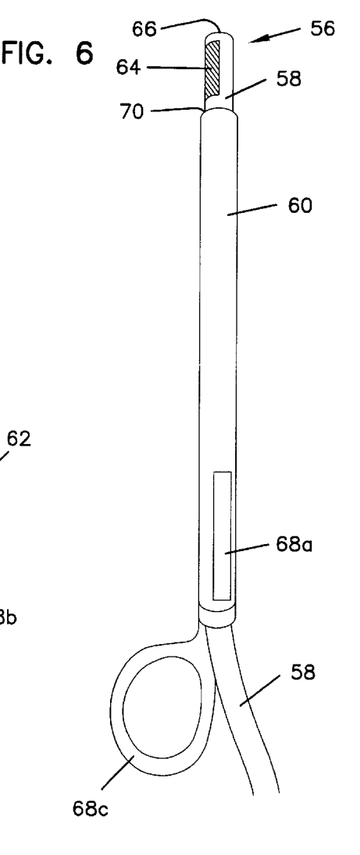
FIG. 6 is another perspective view of the apparatus of FIG. 5.

In FIG. 5, the apparatus 56 includes a flexible member 58, a retaining member 60, and a control member 62. The miniaturized ultrasound transducer 64 is mounted on the flexible member 58 proximate a distal end 66 of the flexible member 58. The retaining member 60 retains the flexible member 58. The control member 62 is coupled to the retaining member 60 and is operable to move the retained flexible member 58 and the ultrasound transducer 64 to optimize ultrasound visualization. As shown, the apparatus 56 is operated by a plurality of handles 68a, b, c and an articulation mechanism 69.

As shown in FIGS. 5–10, the retaining member 60 is a semi-rigid tube, e.g. relatively more rigid than the flexible member 58. The flexible member 58 is inserted through and retained by the retaining member 60, and the ultrasound transducer 64 is exposed at an end 70 of the retaining member 60. The control member 62 includes the plurality of handles 68a, b, c, and the articulation mechanism 69. The articulation mechanism 69 is connected to the handles 68a, b, c and the flexible member 58, and the handles are operable to control the movements of the flexible member 58 and the ultrasound transducer 64.

Figures 9, 10:
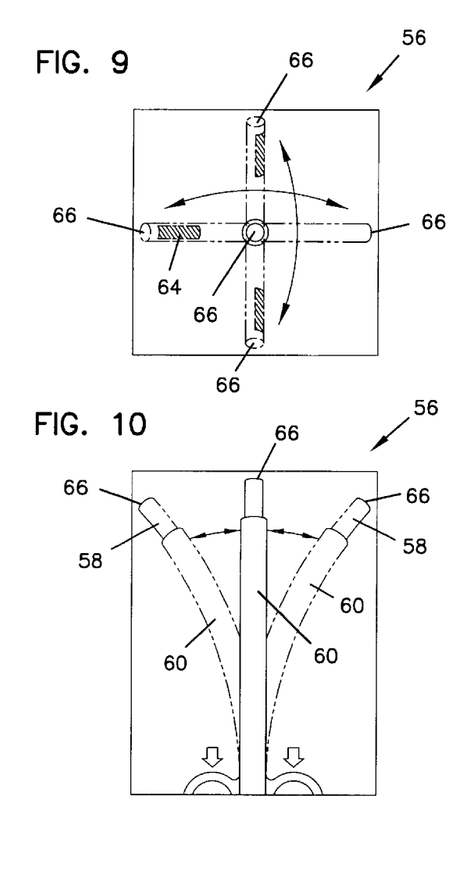
FIG. 9 is a top view of the apparatus of FIG. 5 showing different operational positions of the apparatus.
FIG. 10 is a side view of the apparatus of FIG. 5 showing different operational positions of the apparatus.

The articulation mechanism 69 can be any conventional mechanism known to the mechanical art. For example, the articulation mechanism 69 may include a plurality of deflecting wires 72 wherein one end of a deflecting wire 72 is attached to the corresponding handle, and the other end of the deflecting wire 72 is attached to the retaining member 60 proximate at the end 70 of the retaining member 60 or the flexible member 58. The handles 68a, b, c, are configured and arranged to pull the deflecting wires 72. As a result, the retaining member 60 bends toward a specific direction. As shown in FIGS. 9 and 10, when the handles 68a, b, c pull the deflecting wires 72 in different ways, the flexible member 58 and the ultrasound transducer 64 bend towards different directions to optimize ultrasound visualization.

Figures 7, 8:
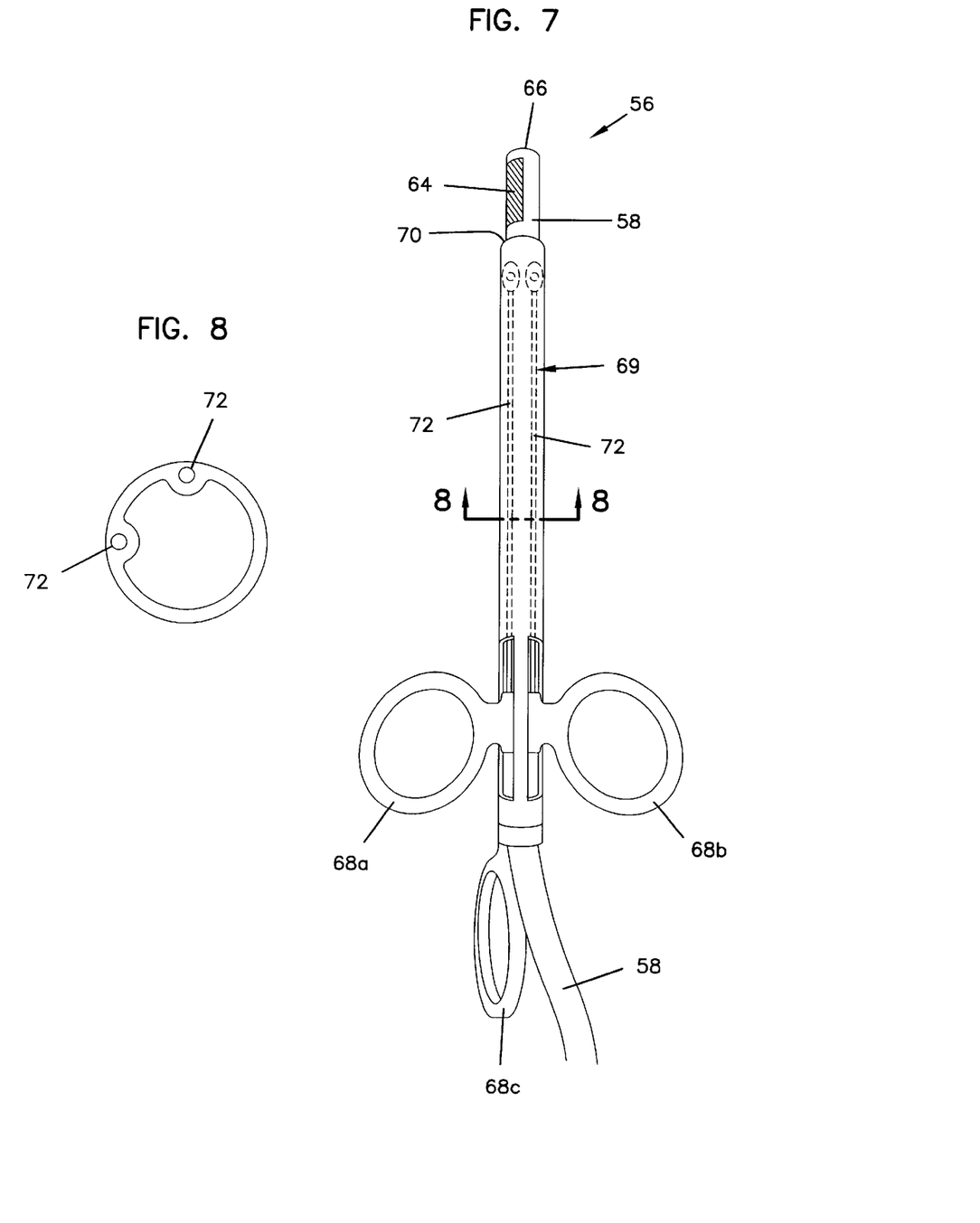
FIG. 7 is a perspective view of the apparatus of FIG. 5 showing an internal articulation mechanism.
FIG. 8 is a cross-sectional view of the apparatus of FIG. 7 along line 8—8.

As shown in FIG. 8, the deflecting wires 72 of the articulation mechanism 69 are inserted through and are retained within the retaining member 60. It is appreciated that the articulation mechanism can be implemented in a variety of ways without departing from the principles of the present invention. For example, more than one deflecting wires can be attached to one handle, etc. It is also appreciated that the control member 62 may include more or less number of handles, or the handles may be placed in different positions to obtain other orientations, within the scope of the present invention.

In an exemplary use of the apparatus 56, one would place the fingers at the handles and control the articulation mechanism 69 by manipulating the handles to optimize ultrasound visualization in confined spaces.

FIGS. 11–14 illustrate a third embodiment of an apparatus 74 for holding and manipulating a miniaturized ultrasound transducer 76 in accordance with the principles of the present invention.

Figure 11:
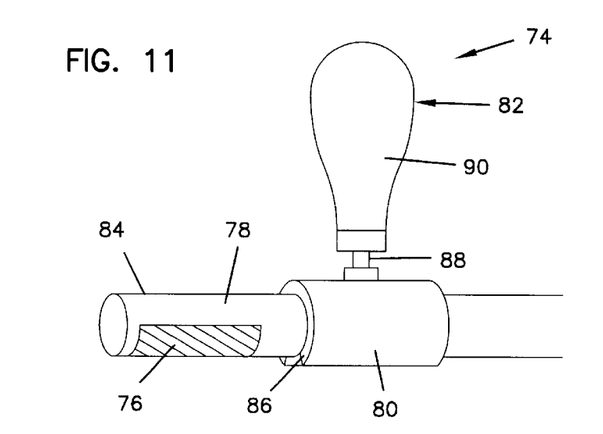
FIG. 11 is a partial perspective view of a third embodiment of an apparatus for holding and manipulating a miniaturized ultrasound transducer in accordance with the principles of the present invention.

In FIG. 11, the apparatus 74 includes a flexible member 78, a retaining member 80, and a control member 82. The miniaturized ultrasound transducer 76 is mounted on the flexible member 78. proximate a distal end 84 of the flexible member 78. The retaining member 80 retains the flexible member 78. The control member 82 is coupled to the retaining member 80 and is operable to move the retained flexible member 78 and the ultrasound transducer 76 to optimize ultrasound visualization.

As shown in FIGS. 11–14, the retaining member 80 is a hollow tube. The flexible member 78 is inserted through and retained by the hollow tube 80, and the ultrasound transducer 76 is exposed at an end 86 of the hollow tube 80. The control member 82 includes a multi-faceted articulated joint 88 and a handle 90. The handle 90 is connected to the multi-faceted articulated joint 88 and is operable to control the positions of the flexible member 78 and the ultrasound transducer 76.

Figure 12:
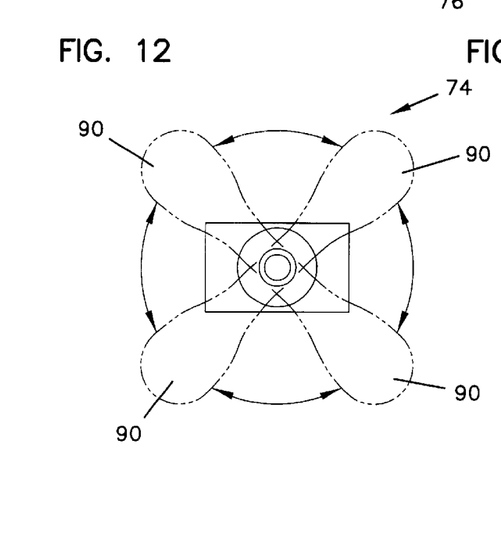
FIG. 12 is a top view of the apparatus of FIG. 11 showing different operational positions of the apparatus.
Figure 13:
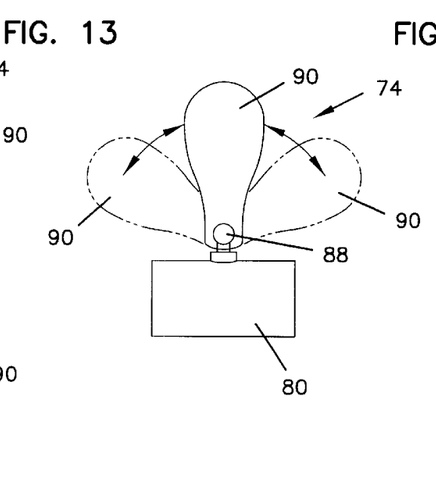
FIG. 13 is a side view of the apparatus of FIG. 11 showing different operational positions of the apparatus.

As shown in FIGS. 12–13, the handle 90 is held by an operator which enables repositioning of the flexible member 78 and the ultrasound transducer 76 by advancing, rotating, and angulating the handle 90. The flexible member 78 is deformable permitting improved ultrasound transducer repositioning.

Figure 14:
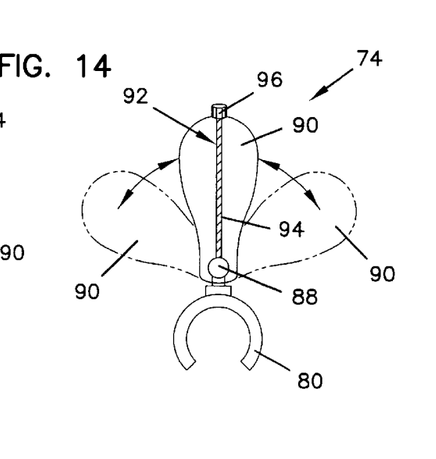
FIG. 14 is a front view of the apparatus of FIG. 11 showing different operational positions of the apparatus.

In FIG. 14, a locking mechanism 92 permits fixation of the handle 90 in a desired position for a given situation. As shown, the locking mechanism 92 includes a deflecting cable or wire 94 and a cap 96. The cap 96 is designed to allow tightening and loosening of the deflecting cable or wire 94 so as to deform the flexible member 78 permitting improved ultrasound transducer repositioning. It is appreciated that any other locking mechanism may be used without departing from the present invention.

Figure 15:
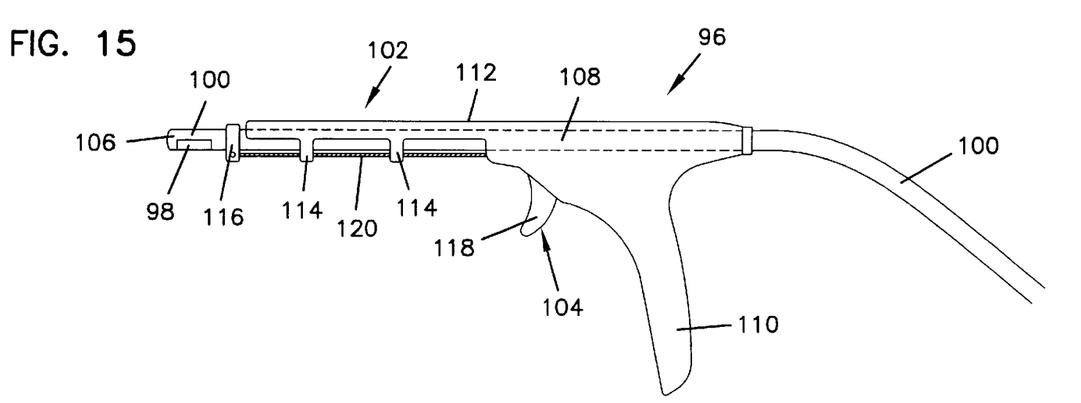
FIG. 15 is a side view of a fourth embodiment of an apparatus for holding and manipulating a miniaturized ultrasound transducer in accordance with the principles of the present invention.
Figure 16:
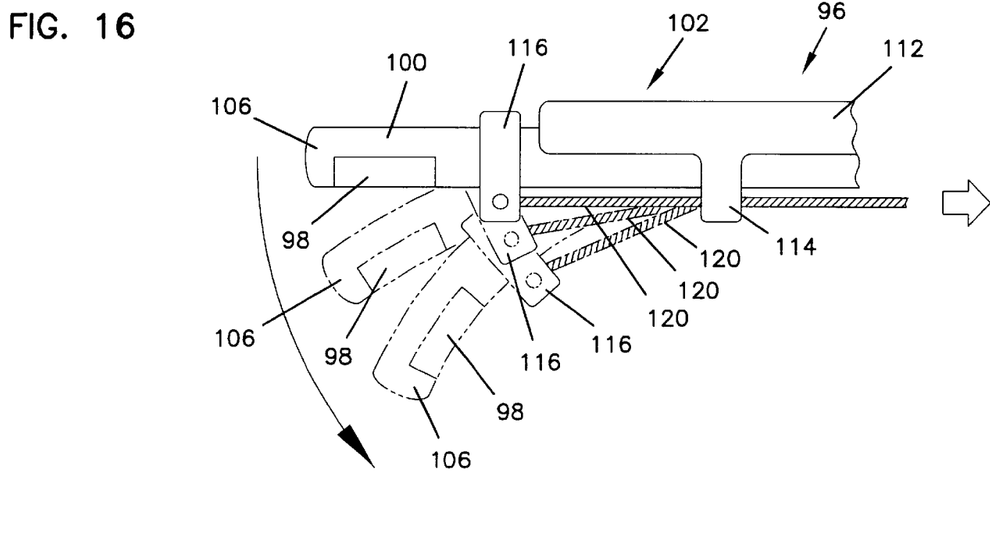
FIG. 16 is an enlarged partial side view of the apparatus of FIG. 15 showing different operational positions of the apparatus.

FIGS. 15–16 illustrate a fourth embodiment of an apparatus 96 for holding and manipulating a miniaturized ultrasound transducer 98 in accordance with the principles of the present invention.

In FIG. 15, the apparatus 96 includes a flexible member 100, a retaining member 102, and a control member 104. The miniaturized ultrasound transducer 98 is mounted on the flexible member 100 proximate a distal end 106 of the flexible member 100. The retaining member 102 retains the flexible member 100. The control member 104 is coupled to the retaining member 102 and is operable to move the retained flexible member 100 and the ultrasound transducer 98 to optimize ultrasound visualization.

In FIGS. 15–16, the retaining member 102 includes a hollow tube 108, a handle 110, a rigid shaft 112, and a plurality of clips 114. The flexible member 100 is inserted through the hollow tube 108 within the handle 110 and is held in position by the clip 114 affixed to the rigid shaft 112. The control member 104 includes a trigger mechanism. The trigger mechanism 104 is connected to the flexible member 100 and is operable to control the movements of the flexible member 100 and the ultrasound transducer 98. Accordingly, the trigger mechanism 104 permits flexion of the flexible member 100 and the ultrasound transducer 98 so as to optimize ultrasound visualization.

The trigger mechanism 104 includes a connector 116, a trigger 118, and a deflecting cable or wire 120. The trigger mechanism 104 is connected to the flexible member 100 via the connector 116. One end of the deflecting cable or wire 120 is connected to the connector 116, and the other end of the deflecting cable or wire 120 is connected to the trigger 118. When the trigger 118 is pulled, the deflecting cable or wire 120 is tightened, as shown in FIG. 16. The connector 116 pulls the distal end 106 of the flexible member 100 in a bent position, e.g. a downward position as shown. It is appreciated that any other trigger mechanism may be used to move the ultrasound transducer to optimize ultrasound visualization without departing from the present invention.

Figure 17:
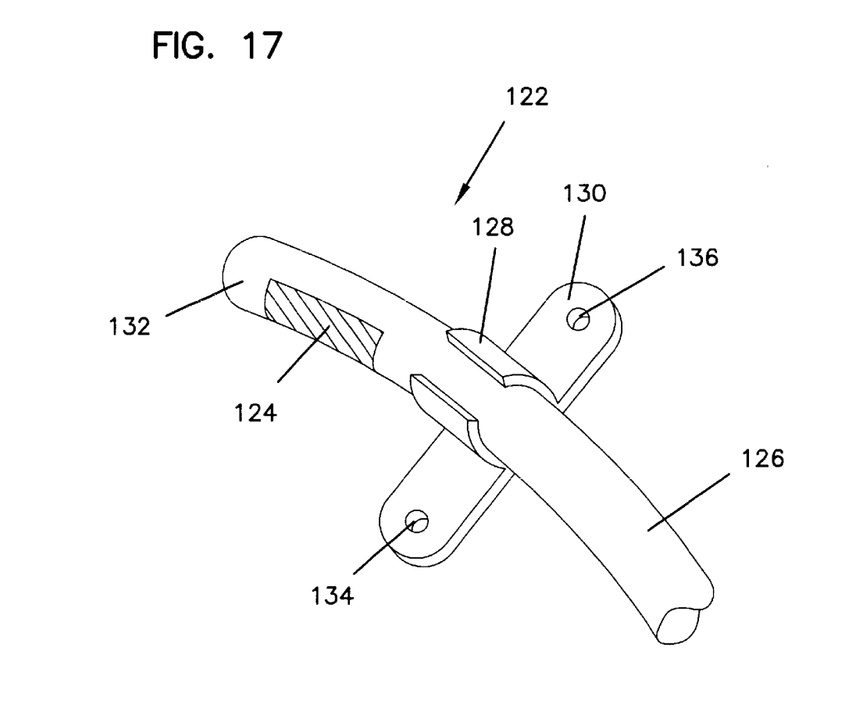
FIG. 17 is a perspective view of a fifth embodiment of an apparatus for holding and manipulating a miniaturized ultrasound transducer in accordance with the principles of the present invention.
Figure 18:
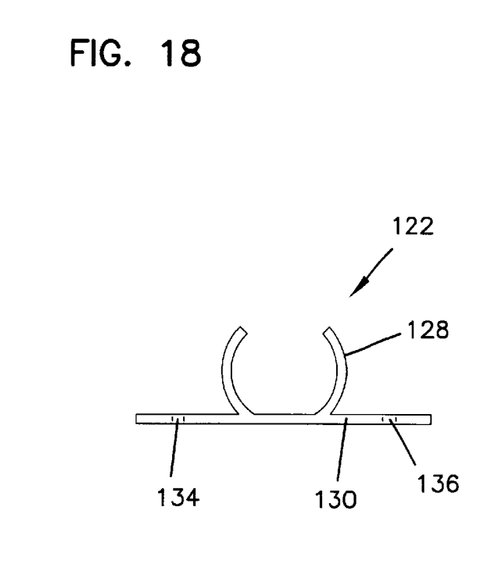
FIG. 18 is a front view of the apparatus of FIG. 17.

FIGS. 17–18 illustrate a fifth embodiment of an apparatus 122 for holding and manipulating a miniaturized ultrasound transducer 124 in accordance with the principles of the present invention.

In FIG. 17, the apparatus 122 includes a flexible member 126, a retaining member 128, and a control member 130. The miniaturized ultrasound transducer 124 is mounted on the flexible member 126 proximate a distal end 132 of the flexible member 126. The retaining member. 128 retains the flexible member 126. The control member 130 is integral to the retaining member 128.

In FIGS. 17–18, the retaining member 128 is a clip having a C shape. The flexible member 126 is inserted into the clip 128. The control member 130 includes a pair of suture holes 134, 136 for fixing the retaining member 128 onto a surface, such as a probe, a blood vessel, etc. The transducer 124 can be removed from the clip 128 without removing the clip 128 from the surface to which the clip 128 is sutured. The flexible member 126 can thus be repositioned and/or rotated at will.

Accordingly, the present invention meets the need to incorporate small devices into the surgical environment. For example, currently a mitral valve is surgically repaired by placing a patient on heart-lung by-pass and removing the blood from the cardiac chambers. A surgeon then visually performs a planned operation under direct visual control. The present invention instead allows the surgeon to operate within the blood containing cardiac chambers using ultrasound as a visual substitute and to take the surgical tools to a specified function. The small attached or incorporated ultrasound transducer is physically controlled in accordance with the present invention as described above.

It is appreciated that the present invention provides an apparatus for holding small or minute ultrasound imaging transducers. The holding apparatus is preferably designed to hold the ultrasound imaging transducers having a diameter less than 5 mm, more preferably having a size that is less than 4 mm in thickness/width and less than 10 mm in length, i.e. a transducer dimension less than 4 mm×4 mm×10 mm.

Also, it is appreciated that various apparatuses, such as rings, clamps, inserting tubes, articulations, etc., can be used for holding the small or minute ultrasound imaging transducers within the scope of the present invention. These apparatuses enable an operator to manipulate small ultrasound imaging devices or devices accommodating ultrasound to foster appropriate functionality within the operating environment. Further, these apparatuses can be used on the surface or within the cavities, vessels or parenchyma of an organ.

Having described the present invention in a preferred embodiment, modifications and equivalents may occur to one skilled in the art. It is intended that such modifications and equivalents shall be included within the scope of the claims which are appended hereto.

What is claimed is:

1. An apparatus for holding and manipulating a miniaturized ultrasound transducer, comprising:

a flexible member having a distal end, whereby proximate the distal end of the flexible member being mountable for the miniaturized ultrasound transducer;

a retaining member retaining the flexible member proximate the distal end of the flexible member;

a control member, coupled to the retaining member, being operable to move the retained flexible member and ultrasound transducer to optimize ultrasound visualization; and the retaining member includes a hollow tube, a handle, a rigid shaft, and a clip, the flexible member is inserted through the hollow tube within the handle and is held in position by the clip affixed to the rigid shaft, the control member includes a trigger mechanism having a trigger and a wire, and the wire is connected to the flexible member and the trigger, the trigger is operable to control the movements of the flexible member and the ultrasound transducer.

2. The apparatus for holding and manipulating a miniaturized ultrasound transducer according to claim 1, wherein the wire is connected proximate the distal end of the flexible member.

3. The apparatus for holding and manipulating a miniaturized ultrasound transducer according to claim 1, wherein the wire is connected to the flexible member through a connector.

4. The apparatus for holding and manipulating a miniaturized ultrasound transducer according to claim 1, wherein the trigger is pullable to tighten the wire so as to deflect at least a portion of the flexible member from a substantially non-deflected position to a deflected position.

5. The apparatus for holding and manipulating a miniaturized ultrasound transducer according to claim 4, wherein the deflected position is a downward position.

6. A method of holding and manipulating a miniaturized ultrasound transducer, comprising the steps of:

providing a flexible member, the miniaturized ultrasound transducer being mounted on the flexible member proximate the distal end of the flexible member;

retaining the flexible member in a retaining member proximate the distal end of the flexible member;

moving the retained flexible member and ultrasound transducer in various directions to optimize ultrasound visualization by a control member, the control member being coupled to the retaining member;

wherein the step of moving the retained flexible member and ultrasound transducer includes the steps of:

providing the retaining member with a hollow tube, a handle, a rigid shaft, and a clip, the flexible member being inserted through the hollow tube within the handle and being held in position by the clip affixed to the rigid shaft; and providing the control member with a trigger mechanism having a trigger and a wire, the wire being connected to the flexible member and the trigger; and pulling the trigger in different degrees.

7. The method of holding and manipulating a miniaturized ultrasound transducer, according to claim 6, wherein the step of pulling the trigger in different degrees comprises tightening the wire and deflecting at least a portion of the flexible member from a substantially non-deflected position to a deflected position.

* * * * *